United States Patent [19]
Koga et al.

[11] Patent Number: 5,583,154
[45] Date of Patent: Dec. 10, 1996

[54] METHOD FOR ENHANCING HAIR GROWTH

[75] Inventors: Hiroyasu Koga; Kazuo Kanai, both of Osaka; Masanori Yoshida, Wakayama, all of Japan

[73] Assignee: Nihon Nohyaku Co., Ltd., Tokyo, Japan

[21] Appl. No.: 389,658

[22] Filed: Feb. 16, 1995

[51] Int. Cl.⁶ .................... A01N 43/02; A61K 31/33
[52] U.S. Cl. .................. 514/449; 514/880; 549/30
[58] Field of Search ................... 514/449, 880; 549/30

[56] References Cited

U.S. PATENT DOCUMENTS

| | | | |
|---|---|---|---|
| 4,118,506 | 10/1978 | Taninaka et al. | 424/277 |
| 4,711,775 | 12/1987 | Dittmar et al. | 424/70 |
| 5,153,126 | 10/1992 | Schroder et al. | 435/134 |

FOREIGN PATENT DOCUMENTS

| | | | |
|---|---|---|---|
| 644978 | 1/1993 | Australia | A61K 31/385 |
| 3182893 | 7/1993 | Australia | A61K 31/385 |
| 0170748A1 | 8/1984 | European Pat. Off. | A61K 7/06 |
| 54-43506 | 12/1979 | Japan | C07D 339/06 |
| 63-66287 | 12/1988 | Japan | A61K 31/385 |
| 672871 | 3/1994 | Japan | A61K 31/385 |

OTHER PUBLICATIONS

Mitchison et al., "The Results of a Randomized Double Blind Controlled Trial Evaluating Malotilate in Primary Bilary Cirrhosis", vol. 17(2), 1993, pp. 227–235.

*Primary Examiner*—Paul J. Killos
*Assistant Examiner*—Rosalynd A. Williams
*Attorney, Agent, or Firm*—Sughrue, Mion, Zinn Macpeak & Seas

[57] ABSTRACT

A composition for enhancing hair growth which comprises a compound represented by the following formula (I) as an active ingredient:

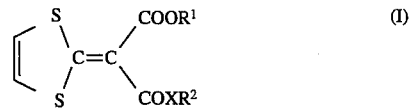

wherein $R^1$ represents an alkyl group having 1 to 8 carbon atoms, $R^2$ represents an alkyl group having 1 to 10 carbon atoms, an alkenyl group having 2 to 6 carbon atoms or a cycloalkyl group having 3 to 8 carbon atoms and X represents —O— or —NH— and a carrier or diluent acceptable for topical composition.

The composition for enhancing hair growth of the present invention has a hair growth enhancing activity and therefore is useful as a hair growth preparation.

1 Claim, 1 Drawing Sheet

METHOD FOR ENHANCING HAIR GROWTH

FIELD OF THE INVENTION

This invention relates to a composition for enhancing hair growth which comprises a compound represented by the following formula (I) as an active ingredient:

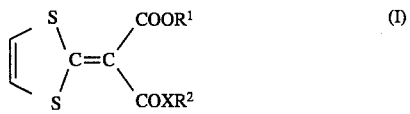

wherein $R^1$ represents an alkyl group having 1 to 8 carbon atoms, $R^2$ represents an alkyl group having 1 to 10 carbon atoms, an alkenyl group having 2 to 6 carbon atoms or a cycloalkyl group having 3 to 8 carbon atoms and X represents —O— or —NH—.

BACKGROUND OF THE INVENTION

Compositions for enhancing hair growth blended with various medicinal components have been known in the prior art. For example, those which are blended with vasodilators, metabolism enhancers, bactericides, keratolytic drugs, hormones, vitamins and the like are currently used for the prevention and treatment of alopecia.

Though these compositions are said to be effective in preventing and treating dandruff, itch, falling hair and the like and in enhancing generation and growth of hair, such effects are not satisfactory yet.

SUMMARY OF THE INVENTION

With the aim of overcoming the aforementioned problems involved in the prior art, the inventors of the present invention have conducted intensive studies on substances having hair growth enhancing activity and found that a compound represented by the following formula (I) can show excellent hair revitalization effect. The present invention has been accomplished on the basis of this finding.

According to the present invention, there is provided a composition for enhancing hair growth which comprises a compound represented by the following formula (I) as an active ingredient:

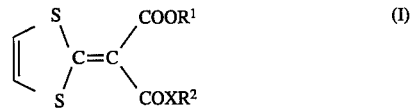

wherein $R^1$ represents an alkyl group having 1 to 8 carbon atoms, $R^2$ represents an alkyl group having 1 to 10 carbon atoms, an alkenyl group having 2 to 6 carbon atoms or a cycloalkyl group having 3 to 8 carbon atoms and X represents —O— or —NH— and a carrier or diluent acceptable for topical composition.

Other objects and advantages of the present invention will be made apparent as the description progresses.

BRIEF DESCRIPTION OF DRAWING

In FIG. 1, - △ -, -○ - and -● - mean vehicle control, PDG and test compound (Compound No. 2), respectively. # and ## mean p<0.05 and p<0.01, respectively vs vehicle control by Mann-Whlteney U test.

DETAILED DESCRIPTION OF THE INVENTION

Figure 1:
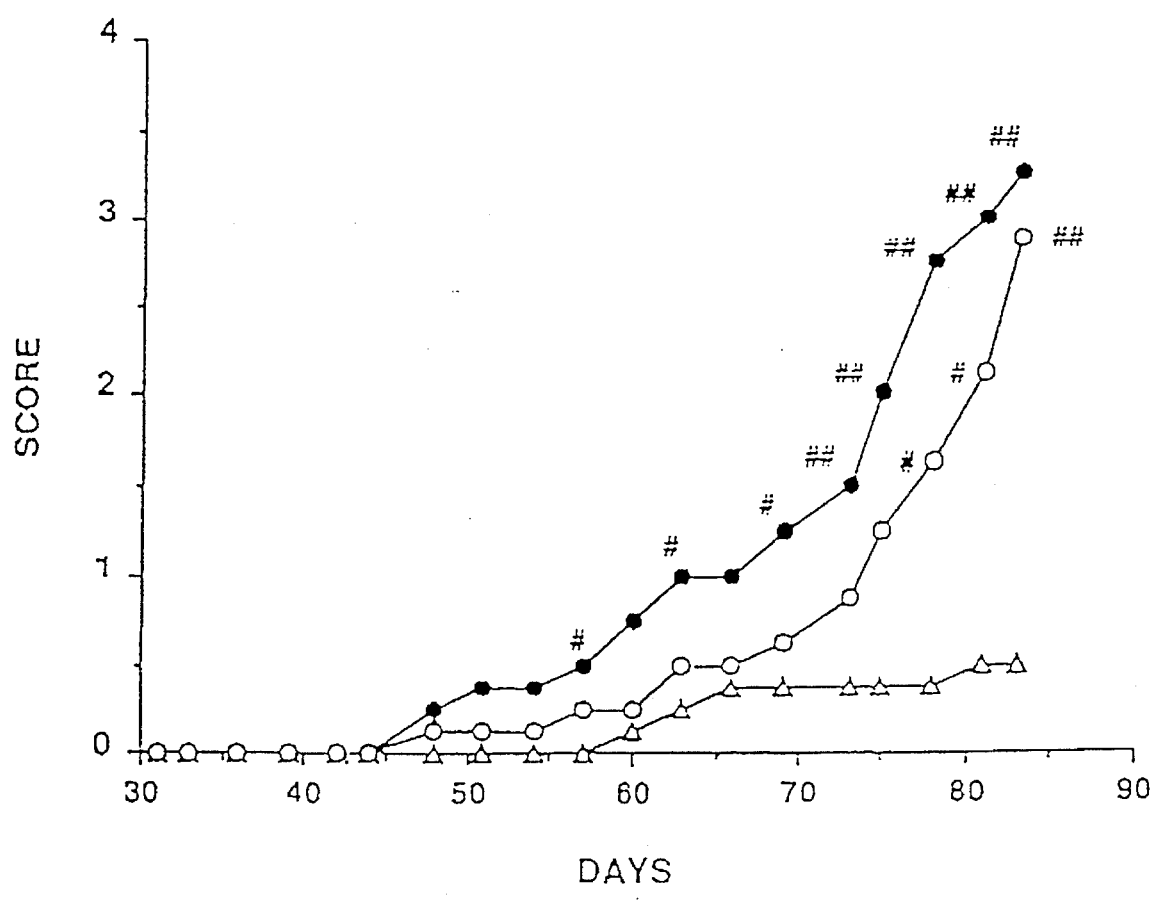
FIG. 1 shows hair growth promoting effect of the test compound and control compound.

The compound represented by the formula (I) to be used as the active ingredient of the present invention have been disclosed as a hepatic disease remedy in U.S. Pat. No. 4,118,506, as an agricultural and horticultural bactericide in JP-B-54-43506 (the term "JP-B" as used herein means an "examined Japanese patent publication"), as a carcinostatic drug in JP-B-63-66287, as a metastasis inhibitor in JP-A-6-72871 (the term "JP-A" as used herein means an "unexamined published Japanese patent application") and as a composition for acceleratiiong wound healing in AU Patent 644,978. A compound for enhancing hair growth represented by the following formula:

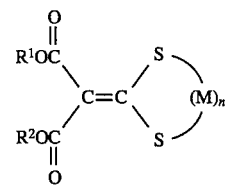

is disclosed in EP 170748A1 corresponding to JP-A-63-10131. However, a sufficient effect could not be obtained by this compound since this compound is unstable and is decomposed in use.

In the formula (I), illustrative examples of the alkyl group having 1 to 8 carbon atoms include methyl, ethyl, n-propyl, i-propyl, n-butyl, i-butyl, n-pentyl, n-hexyl and the like groups, illustrative examples of the alkyl group having 1 to 10 carbon atoms include methyl, ethyl, n-propyl, i-propyl, n-butyl, i-butyl, n-pentyl, n-hexyl, n-heptyl, n-octyl, n-decyl and the like groups, illustrative examples of the alkenyl group having 2 to 6 carbon atoms include vinyl, allyl, 2-butenyl, 3-pentenyl and the like groups and illustrative examples of the cycloalkyl group having 3 to 8 carbon atoms include cyclopropyl, cyclopentyl, cyclohexyl, cycloheptyl and the like groups. Each of $R^1$ and $R^2$ is preferably an alkyl group having 1 to 6 carbon atoms and X is oxygen. Preferred examples of the compound include diisopropyl 1,3-dithiol-2-ylidenemalonate.

Next, typical examples of the compounds to be used in the present invention, though not particularly limited, are shown in Table 1.

TABLE 1

| No. | $R^1$ | $XR^2$ | Physical property |
|---|---|---|---|
| 1 | $CH_3$ | $OCH_3$ | m.p. 125–129° C. |
| 2 | i-$C_3H_7$ | O-i-$C_3H_7$ | m.p. 59–60° C. |
| 3 | i-$C_3H_7$ | $O-C_2H_5$ | m.p. 54° C. |
| 4 | i-$C_3H_7$ | O-cyclopentyl | m.p. 68–69° C. |
| 5 | i-$C_3H_7$ | O-n-$C_6H_{13}$ | m.p. 40° C. |
| 6 | i-$C_3H_7$ | $O-CH_2CH=CH_2$ | m.p. 48° C. |
| 7 | i-$C_3H_7$ | NH-cyclopropyl | m.p. 70–72° C. |
| 8 | i-$C_3H_7$ | NH-n-$C_6H_{13}$ | $n_D^{23}$ 1.5728 |
| 9 | $CH_3$ | O-i-$C_4H_9$ | $n_D^{20}$ 1.5928 |
| 10 | $C_2H_5$ | $OC_2H_5$ | m.p. 113° C. |
| 11 | i-$C_4H_9$ | O-i-$C_4H_9$ | m.p. 76–78° C. |

TABLE 1-continued

| No. | $R^1$ | $XR^2$ | Physical property |
|-----|-------|--------|-------------------|
| 12 | i-$C_5H_{11}$ | O-i-$C_5H_{11}$ | m.p. 55–56° C. |
| 13 | n-$C_3H_7$ | O-n-$C_3H_7$ | m.p. 73–75° C. |
| 14 | n-$C_4H_9$ | O-n-$C_4H_9$ | m.p. 74–75° C. |
| 15 | s-$C_4H_9$ | O-s-$C_4H_9$ | m.p. 63–65° C. |
| 16 | n-$C_5H_{11}$ | O-n-$C_5H_{11}$ | m.p. 70–70.5° C. |

The composition for enhancing hair growth of the present invention may be made in the usual way into conventional preparation forms such as hair tonic, hair lotion, hair cream, ointment, shampoo, rinse and the like by blending with a carrier or diluent acceptable for topical composition.

Alcohols, oils and fats, surface active agents and the like may be used as blending base materials, and vasodilators, bactericides, keratolytic drugs, metabolism enhancers, hormones, vitamins and the like may also be blended as other effective components, as well as menthol and the like perfumes.

According to the present invention, amount of the active ingredient to be blended may be optionally selected within the range of generally from 0.01 to 10%, preferably 0.1 to 5% by weight based on the total amount of the composition.

The following synthesis examples, examples and test example are provided to further illustrate the present invention. It is to be understood, however, that the examples are for purpose of illustration only and are not intended as a definition of the limits of the invention.

Examples of the synthesis of the compound of formula (I) are shown in the following.

SYNTHESIS EXAMPLE 1

Dimethyl 1,3-dithiol-2-ylidenemalonate (compound No. 1)

A 5.28 g portion of dimethyl malonate (0.04 mol) and 3.66 g of carbon disulfide (0.048 mol) were dissolved in 25 ml of dimethyl sulfoxide, 10.9 g of 45% potassium hydroxide aqueous solution was added dropwise to the solution which was cooled in an ice bath, and the resulting mixture was stirred for 20 minutes at room temperature. The obtained reaction solution was added dropwise to a mixture solution consisting 19.6 g of 40% chloroacetaldehyde and 2.88 g of glacial acetic acid, which was cooled at a temperature of 5° C. or lower, and the mixture was stirred for 30 minutes at the same temperature. The reaction solution was poured into ice water, extracted twice with ethyl acetate and then washed with water. After drying on magnesium sulfate, the solvent was removed by distillation under a reduced pressure to obtain 4-hydroxy-1,3-dithiol-2-ylidenemalonate. The obtained compound and 12.2 g of triethylamine (0.12 mol) were dissolved in 20 ml of dioxane to which was then gradually added dropwise 6.9 g of methanesulfonyl chloride (0.06 mol) at 0° C. After completion of the dropwise addition, the resulting mixture was stirred for 10 minutes at room temperature and then heated under reflux for 10 minutes. The reaction solution was poured into ice water, extracted with ethyl acetate and then washed with water. After drying on magnesium sulfate, the solvent was removed by distillation under a reduced pressure, and the resulting residue was purified by a silica gel column chromatography (n-hexane:ethyl acetate=2:1) to obtain 4.0 g of the title compound in the form of crystals having a melting point of 125° to 129° C. (yield, 43%).

SYNTHESIS EXAMPLE 2

Ethyl isopropyl 1,3-dithiol-2-ylidenemalonate (compound No. 3)

A 14.4 g portion of diisopropyl 1,3-dithiol-2-ylidenemalonate (0.05 mol) was dissolved in 50 ml of isopropanol, 2.95 g of potassium hydroxide (0.05 mol) was added to the solution at 30° C., and the resulting mixture was stirred for 1 hour. The solution was acidified with 6N hydrochloric acid and extracted with 200 ml of methylene chloride and washed with water and saturated brine in that order. After drying on magnesium sulfate, the solvent was removed by distillation under a reduced pressure and the resulting residue was crystallized from ether to obtain 8.5 g of isopropyl hydrogen 1,3-dithiol-2-ylidenemalonate in the form of white crystals (yield, 75%). Then, 2.7 g (0.011 mol) of the obtained crystals and 3.6 g (0.012 mol) of 2-chloro-1methylpyridinium p-toluene sulfonate were dissolved in 20 ml of dichloromethane to which was then added dropwise a dichloromethane solution of 0.51 g (0.011 mol) of ethanol and 3.46 g (0.034 mol) of triethylamine at 10° C., subsequently stirring the resulting mixture for 2 hours at room temperature. The reaction solution was poured into ice water, extracted with dichloromethane and then washed with 2N hydrochloric acid, 10% sodium carbonate aqueous solution and water in that order. After drying on magnesium sulfate, the solvent was removed by distillation under a reduced pressure, and the resulting residue was purified by a silica gel column chromatography (n-hexane:ethyl acetate=2:1) to obtain 1.0 g of the title compound in the form of crystals having a melting point of 54° C. (yield, 35%).

SYNTHESIS EXAMPLE 3

O-Isopropyl N-cyclopropyl 1,3-dithiol-2-ylidenemalonate (compound No. 7)

A 2.46 g portion of isopropyl hydrogen 1,3-dithiol-2-ylidenemalonate (0.01 mol), 0.80 g of cyclopropylamine (0.014 mol) and 3.25 g of diethyl phosphorocyanidate (0.02 mol) were dissolved in 20 ml of dimethylformamide, 3.03 g of triethylamine (0.03 mol) was added dropwise to the solution which was cooled 10° C., and the resulting mixture was stirred for 1 hour at the same temperature and then for 3 hours at room temperature. The reaction solution was poured into ice water, extracted with ethyl acetate and then washed with 1N hydrochloric acid, saturated sodium bicarbonate aqueous solution and water in that order. After drying on magnesium sulfate, the solvent was removed by distillation under a reduced pressure, and the resulting residue was purified by a silica gel column chromatography (ethyl acetate:n-hexane=1:1) to obtain 2.6 g of the title compound in the form of crystals having a melting point of 70° to 72° C. (yield, 91%).

EXAMPLE 1

| | |
|---|---|
| inventive compound | 0.5 g |
| salicylic acid | 1.0 g |
| resorcinol | 2.0 g |
| glycerol | 2.0 g |
| phenol | 1.0 g |
| castor oil | 1.0 g |
| lavender oil | 10.0 ml |

A lotion of 100 ml in total volume was prepared by dissolving the above components in ethanol.

EXAMPLE 2

| inventive compound | 1.0 g |
|---|---|
| peppermint oil | 0.6 g |
| glycerol | 15.0 ml |
| lavender oil | 10.0 ml |

A lotion of 100 ml in total volume was prepared by dissolving the above components in ethanol.

EXAMPLE 3

| inventive compound | 0.1 g |
|---|---|
| calamine | 8.0 g |
| sodium alginate | 1.25 g |
| glycerol | 4.0 g |
| methyl parahydroxybenzoate | 0.2 g |
| zinc oxide | 8.0 g |
| Tween 20 | 0.01 g |

A lotion of 100 ml in total volume was prepared by dissolving the above components in purified water.

EXAMPLE 4

| inventive compound | 0.5 g |
|---|---|
| potash soap | 8.0 g |
| peppermint oil | 0.6 g |
| lavender oil | 10.0 ml |

A lotion of 100 ml in total volume was prepared by dissolving the above components in ethanol.

EXAMPLE 5

| inventive compound | 0.5 g |
|---|---|
| ethyl parahydroxybenzoate | 0.025 g |
| propyl parahydroxybenzoate | 0.015 g |
| sodium lauryl sulfate | 1.5 g |
| propylene glycol | 12.0 g |
| stearyl alcohol | 22.0 g |
| white vaseline | 25.0 g |
| purified water | 38.96 g |

An ointment of 100 g in total weight was prepared by dissolving and mixing the above components.

EXAMPLE 6

| inventive compound | 0.5 g |
|---|---|
| polyethylene glycol 400 | 57.5 g |
| polyethylene glycol 1500 | 20.0 g |
| polyethylene glycol 4000 | 22.0 g |

An ointment of 100 g in total weight was prepared by dissolving and mixing the above components.

EXAMPLE 7

| inventive compound | 0.5 g |
|---|---|
| purified lanolin | 5.0 g |
| white beeswax | 5.0 g |
| white vaseline | 89.5 g |

An ointment of 100 g in total weight was prepared by dissolving and mixing the above components.

TEST EXAMPLE

Male mice of C3H strain at the telogen phase of hair-cycle were clipped on back and divided into test groups of 8 animals each. Test compound (Compound No. 2) was dissolved in 70% (v/v) ethanol. Pentadecanoic acid monoglyceride (PDG) was used as a positive control to 3% (w/v) test solution in the vehicle (70% (v/v) ethanol) was topically applied to the dorsal skin of the mice daily at the volume of 0.1 ml/mouse/day. The vehicle control group was given in the same volume of vehicle alone. Hair growth promoting effect of the test compound was evaluated according to the scale shown in Table 2, with the results shown in FIG. 1.

As shown in FIG. 1, in comparison with the vehicle control group, significant promotion of hair growth was observed in the test group animals applied with the present invention. Further, in comparison with the PDG which is known as hair growth promoting agent, the present invention showed more potent effect on the hair growth.

TABLE 2

| Score of hair growth | |
|---|---|
| Score | Criterion |
| 0 | Hairless (telogen phase) |
| 1 | Hair growth was observed (Hair cycle was hanged to Anagen phase) |
| 2 | ≧25% of dorsal skin area was covered with regrowth-hair |
| 3 | ≧50% of dosal skin area was covered with regrowth-hair |
| 4 | ≧75% of dosal skin area was covered with regrowth-hair |
| 5 | Completely covered with regrowth-hair |

Thus, it is apparent that the composition for enhancing hair growth of the present invention has a hair revitalization enhancing function and therefore is useful as a hair growth enhancing preparation.

While the invention has been described in detail and with reference to specific examples thereof, it will be apparent to one skilled in the art that various changes and modifications can be made therein without departing from the spirit and scope thereof.

What is claimed is:

1. A method for enhancing hair growth which comprises applying a composition for enhancing hair growth to an area where hair growth is desired, wherein the composition comprises a pharmacologically effective amount of a compound represented by the following formula (I) as an active ingredient:

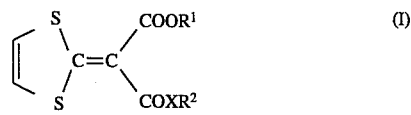

wherein $R^1$ represents an alkyl group having 1 to 8 carbon atoms, $R^2$ represents an alkyl group having 1 to 10 carbon atoms, an alkenyl group having 2 to 6 carbon atoms or a cycloalkyl group having 3 to 8 carbon atoms and X represents —O— or —NH— and a carrier or diluent acceptable for a topical composition.

* * * * *